US00PP34725P2

(12) United States Plant Patent
Post

(10) Patent No.: US PP34,725 P2
(45) Date of Patent: Nov. 8, 2022

(54) ***CHRYSANTHEMUM* PLANT NAMED 'DLFSKAT5'**

(50) Latin Name: ***Chrysanthemum* X *morifolium***
Varietal Denomination: DLFSKAT5

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/732,515

(22) Filed: Apr. 29, 2022

Related U.S. Application Data

(60) Provisional application No. 63/182,480, filed on Apr. 30, 2021.

(51) Int. Cl.
*A01H 5/02* (2018.01)
*A01H 6/14* (2018.01)

(52) U.S. Cl.
USPC ..... Plt./289

(58) Field of Classification Search
USPC ..... Plt./263.1, 286, 287, 289
See application file for complete search history.

*Primary Examiner* — Karen M Redden
(74) *Attorney, Agent, or Firm* — C. Anne Whealy

(57) ABSTRACT

A new and distinct cultivar of *Chrysanthemum* plant named 'DLFSKAT5', characterized by its upright plant habit; uniform growth habit; vigorous growth habit and rapid growth rate; durable dark green-colored leaves; strong upright flowering stems; incurved decorative-type inflorescences with bright yellow green-colored ray florets; relative tolerance to low and high production temperatures; and good postproduction longevity.

2 Drawing Sheets

Figure 1:
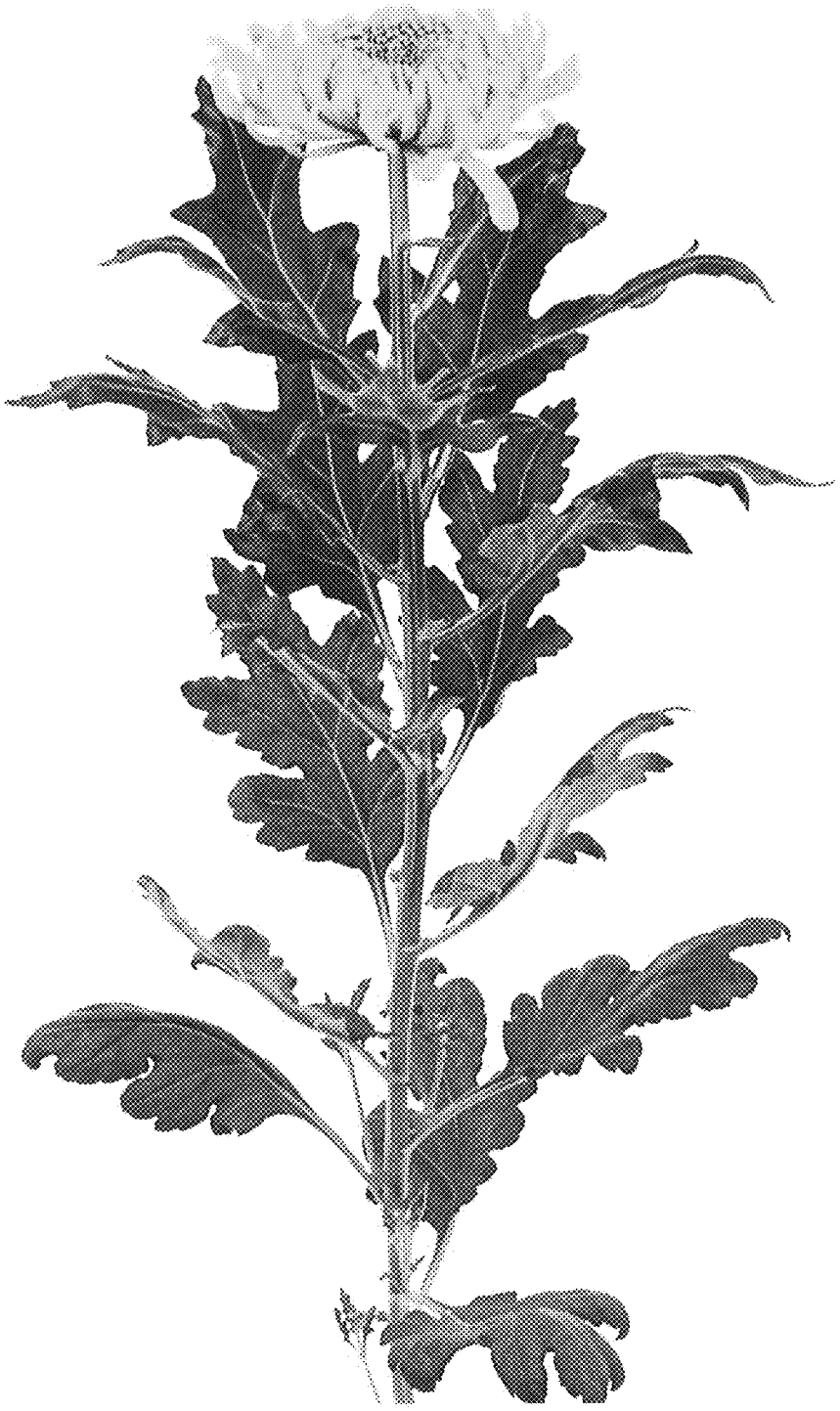

Botanical designation: *Chrysanthemum* X *morifolium*.
Cultivar denomination: 'DLFSKAT5'.

CROSS-REFERENCED TO CLOSELY-RELATED APPLICATIONS

Title: Varieties of *Chrysanthemum* Plants
Inventor/Applicant: Arie Gerard Post
Filed: Apr. 30, 2021
Ser. No.: 63/182,480
Inventor/Applicant hereby claims the priority benefit of this provisional U.S. Patent Application.

STATEMENT REGARDING PRIOR DISCLOSURES BY INVENTOR/APPLICANT & ASSIGNEE

A Japanese Plant Breeder's Rights application for the instant plant was filed by the Assignee, Deliflor Royalties B.V. of Maasdijk, The Netherlands on Jun. 21, 2021, application number 35518. Foreign priority is not claimed to this application.

A Columbian Plant Breeder's Rights application for the instant plant was filed by the Assignee, Deliflor Royalties B.V. of Maasdijk, The Netherlands on Jul. 12, 2021, application number A212813. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFSKAT5'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in September, 2017 of a proprietary selection of *Chrysanthemum* x *morifolium* identified as code number KR 2014.2773-1, not patented, as the female, or seed, parent with a proprietary selection of *Chrysanthemum* x *morifolium* identified as code number KR 10131, not patented, as the male, or pollen, parent. The new *Chrysanthemum* plant was discovered and selected as a single flowering plant from within the progeny of the stated cross-pollination in a controlled greenhouse environment in Maasdijk, The Netherlands in June, 2018.

Asexual reproduction of the new *Chrysanthemum* plant by vegetative terminal cuttings since June, 2018 has shown that the unique features of this new *Chrysanthemum* plant are stable and reproduced true to type in successive generations of asexual reproduction.

SUMMARY OF THE INVENTION

The following traits have been repeatedly observed and are determined to be the unique characteristics of 'DLFSKAT5'. These characteristics in combination distinguish 'DLFSKAT5' as a new and distinct *Chrysanthemum* plant:

1. Upright plant habit; uniform growth habit.
2. Vigorous growth habit and rapid growth rate.
3. Durable dark green-colored leaves.
4. Strong upright flowering stems.
5. Incurved decorative-type inflorescences with bright yellow green-colored ray florets.
6. Relatively tolerant to low and high production temperatures.
7. Good postproduction longevity.

Plants of the new *Chrysanthemum* differ primarily from plants of the female parent selection in the following characteristics:

1. Plants of the new *Chrysanthemum* have larger inflorescences than plants of the female parent selection.
2. Ray florets of plants of the new *Chrysanthemum* are darker yellow green in color than ray florets of plants of the female parent selection.

Plants of the new *Chrysanthemum* differ primarily from plants of the male parent selection in the following characteristics:

1. Leaves of plants of the new *Chrysanthemum* have acute apices whereas leaves of plants of the male parent selection have rounded apices.
2. Ray florets of plants of the new *Chrysanthemum* are lighter yellow green in color than ray florets of plants of the male parent selection.

Plants of the new *Chrysanthemum* can be compared to plants of *Chrysanthemum* X *morifolium* 'Anastasia Green', disclosed in U.S. Plant Pat. No. 18,032. In side-by-side comparisons, plants of the new *Chrysanthemum* differ primarily from plants of 'Anatasia Green' in inflorescence size as plants of the new *Chrysanthemum* have smaller inflorescences than plants of 'Anastasia Green'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a side perspective view of a typical flowering stem of 'DLFSKAT5' grown as a disbud-type cut flower.

Figure 2:
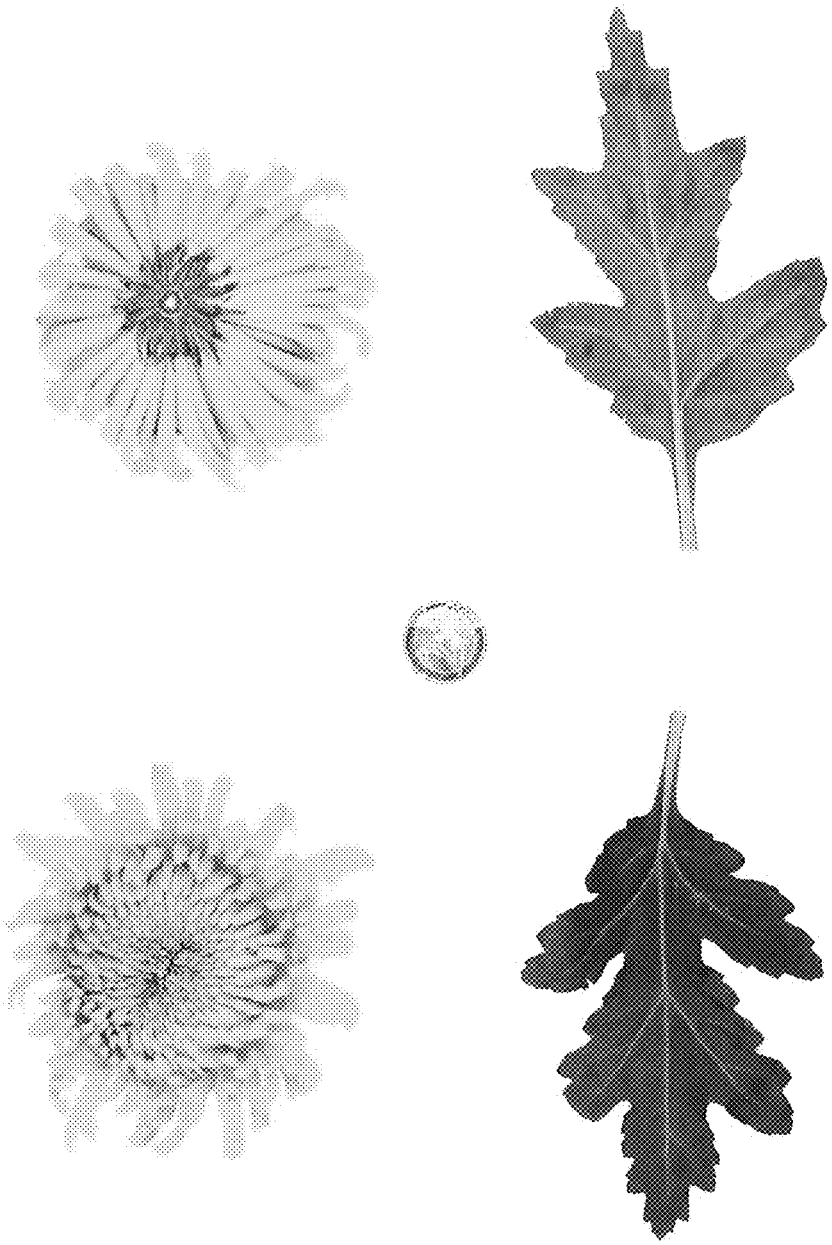

The photograph on the second sheet (FIG. 2) is a close-up view of upper (left) and lower (right) surfaces of typical inflorescences and typical leaves of 'DLFSKAT5'.

DETAILED BOTANICAL DESCRIPTION

The aforementioned photographs and following observations and measurements describe plants grown during the late winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 7 klux. Plants were grown as single-stem disbud-type plants and were eleven weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFSKAT5'.

Parentage:

*Female, or seed, parent*.—Proprietary selection of *Chrysanthemum* x *morifolium* identified as code number KR 2014.2773-1, not patented.

*Male, or pollen, parent*.—Proprietary selection of *Chrysanthemum* x *morifolium* identified as code number KR 10131, not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous incurved decorative-type cut flower that is typically grown as a single stem disbud-type; upright plant habit; vigorous growth habit and rapid growth rate.

*Plant height, soil level to top of foliar plane*.—About 73.3 cm.

*Plant height, soil level to top of inflorescence plane*.—About 75.1 cm.

*Plant (spray) diameter*.—About 32 cm.

*Flowering stem length*.—About 71.2 cm.

*Flowering stem diameter*.—About 9 mm.

*Flowering stem internode length*.—About 2.1 cm.

*Flowering stem strength*.—Strong.

*Flowering stem aspect*.—Erect.

*Flowering stem texture and luster*.—Moderately to densely pubescent; slightly glossy.

*Flowering stem color, developing*.—Close to a blend of 144A and 144B.

*Flowering stem color, developed*.—Close to 146B; at the ridges, close to 148B.

*Leaf description*.—Arrangement: Alternate; simple. Length: About 15.4 cm. Width: About 10.1 cm. Shape, in overall outline: Broadly ovate to broadly elliptic. Apex: Abruptly acute. Base: Attenuate. Margin: Palmately lobed, coarsely dentate to senate; sinuses divergent to parallel and medium to deep in depth; slightly undulate. Texture and luster, upper surface: Moderately pubescent, not rugose; moderately velvety; slightly glossy. Texture and luster, lower surface: Densely pubescent, prominent venation; slightly velvety; slightly glossy. Venation pattern: Pinnate. Color: Developing leaves, upper surface: Close to NN137B. Developing leaves, lower surface: Close to 138B. Fully developed leaves, upper surface: Close to a blend of NN137A, 147A and N189A; venation, close to 146A. Fully developed leaves, lower surface: Close to 147B; venation, close to 146C to 146D. Petioles: Length: About 2.1 cm. Diameter: About 3.5 mm by 5 mm. Strength: Moderately strong. Texture and luster, upper and lower surfaces: Densely pubescent; slightly glossy. Color, upper surface: Close to 147B; edges, slightly darker than 137A. Color, lower surface: Close to 146C; edges, close to 147B. Stipules: Quantity and appearance: Two leafy stipules, opposite, at the petiole attachment to the stem. Length: About 7 mm. Width: About 4.5 mm. Shape: Broadly ovate; apex, short apiculate; base, broadly cuneate; margins, entire. Texture and luster, upper and lower surfaces: Densely pubescent; slightly glossy. Color, upper surface: Close to a blend of NN137A, 147A and N189A. Color, lower surface: Close to 147B.

Inflorescence description:

*Appearance*.—Decorative-type inflorescence form with incurved narrowly oblanceolate tubular ray florets and tubular disc florets; inflorescences, rotate and flattened globular in overall shape; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 55 days later when grown as a disbud-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a disbud-type, only the terminal inflorescence is allowed to develop; plants of the new *Chrysanthemum* are typically not grown as a spray-type, however, if not disbudded, about 19 inflorescence buds will develop per flowering stem.

*Inflorescence size*.—Diameter: About 12.5 cm. Depth (height): About 3.9 cm. Disc diameter: About 2 mm; inconspicuous.

*Receptacles*.—Height: About 8 mm. Diameter: About 1.5 cm. Shape: Broad flattened globular. Color: Close to 145B and 145C.

*Inflorescence buds*.—Height: About 1.8 cm. Diameter: About 2.6 cm. Shape: Flattened ovoid. Texture and luster: Slightly pubescent; slightly glossy. Color: Developing involucral bracts, close to 137B and 138A; developing ray florets, close to N144D to 145A.

*Ray florets*.—Quantity and arrangement: About 440 arranged in about twelve whorls. Length: About 3.9 cm, varying between 1.1 cm and 5.3 cm. Width: About 8 mm, varying between 3 mm and 14 mm. Shape: Incurved narrowly oblanceolate tubular; apices are strongly concave and incurved. Apex: Acute to broadly acute. Base: Fused, tubular. Margin: Entire; not undulate. Aspect: About 45° from vertical. Texture and luster, upper surface: Smooth, glabrous; slightly velvety; matte. Texture and luster, lower surface: Smooth, glabrous; slightly glossy. Color: When opening, upper surface: Close to 154C; towards the apex, close to 150A. When opening, lower surface: Close to 154B; towards the apex, close to 150A. Fully opened, upper surface: Close to 154D; towards the apex, close to 154C; venation, similar to lamina colors; color does not change with subsequent development. Fully opened, lower surface: Close to 150A; venation, close to 150A; color does not change with subsequent development.

*Disc florets*.—Quantity and arrangement: About three randomly arranged at the center of the receptacle; disc florets typically do not completely develop. Length: About 6 mm. Diameter: About 1.5 mm. Shape: Tubular. Apex: Obtuse. Margin, free-part: Entire. Texture and luster, inner and outer surfaces: Smooth, glabrous; glossy. Color, when opening: Towards the apex, close to 144A; mid-section and towards the base, close to 1D; at the base, close to 145D. Color, fully opened: Towards the apex, close to 143B; mid-section, close to 144C; towards the base, close to 155C.

*Involucral bracts*.—Quantity and arrangement: About 46 arranged in about three whorls. Length: About 1.1 cm. Width: About 4 mm. Shape: Narrowly oblong to narrowly ovate. Apex: Bluntly acute. Base: Cuneate. Margin: Entire. Texture and luster, upper surface: Smooth, glabrous; glossy. Texture and luster, lower surface: Moderately pubescent; matte. Color, upper surface: Close to 144A; lateral margins, translucent and close to 157C and apical margins tinged with close to N199A. Color, lower surface: Close to 137B and 138A; lateral margins, translucent and close to 157C and apical margins tinged with close to N199A.

*Peduncles*.—Length: About 3.2 cm. Diameter: About 4 mm. Strength: Strong. Aspect: Upright. Texture and luster: Moderately to densely pubescent; moderately glossy. Color: Close to 138A; at the ridges, close to 138B to 138C.

*Reproductive organs*.—Androecium: To date, stamen development has not been observed on plants of the new *Chrysanthemum*. Gynoecium: Present only on ray florets as disc florets do not fully develop. Quantity: One per floret. Pistil length: About 7 mm. Style length: About 6 mm. Style color: Close to 151D. Stigma diameter: About 1 mm. Stigma shape: Cleft, decurrent. Stigma color: Close to 151B. Ovary color: Close to 157D.

*Seeds and fruits*.—To date, seed and fruit development have not been observed on plants of the new *Chrysanthemum*.

Pathogen & pest resistance: To date, plants of the new *Chrysanthemum* have not been observed to be resistant to pathogens and pests common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFSKAT5' as illustrated and described.

* * * * *